United States Patent [19]

Morgan et al.

[11] Patent Number: 5,453,542

[45] Date of Patent: Sep. 26, 1995

[54] PREPARATION OF 4,6-DIAMINORESORCINOL THROUGH A BISAZOARYLRESORCINOL INTERMEDIATE

[75] Inventors: Ted A. Morgan; Bassam S. Nader; Paul Vosejpka; Weshi Wu, all of Midland, Mich.; Andrew S. Kende, Pittsford, N.Y.

[73] Assignee: The Dow Chemical Company, Midland, Mich.

[21] Appl. No.: 201,297

[22] Filed: Feb. 24, 1994

[51] Int. Cl.$^6$ .................................. C07C 213/02
[52] U.S. Cl. ..................... 564/415; 534/688; 564/442; 564/443
[58] Field of Search ............... 534/688; 564/415, 564/442, 443

[56] References Cited

U.S. PATENT DOCUMENTS

| | | | |
|---|---|---|---|
| 4,766,244 | 8/1988 | Lysenko | 564/418 |
| 4,982,001 | 1/1991 | Lysenko et al. | 564/418 |

OTHER PUBLICATIONS

"Polybenzothiazoles and Polybenxoxazoles" by Paul D. Sybert; printed in vol. 11 *Encyclopedia of Polymer Science and Engineering* ©1988 by John Wiley & Sons, pp. 601–647.

*Advanced Organic Chemistry* 4th Edition by Jerry March ©John Wiley & Sons, p. 1224.

"General Base Catalysis of Orientation in Resorcinol Couplings" by H. F. Hodson et al.; printed in *Helvetica Chimica Acta*, vol. XLI, Fasciculus VI (1958)—Nr. 195, pp. 1816–1823.

"Isomeric Phenyl Dis–Azo Resorcinols" by Liebermann and Kostanecki, printed in *Berichte der Deut Deutschen Chemischen Gesellschaft* ©1988, vol. XX, pp. 3114–3119.

"Some Disazo and Trisazo Derivatives of Resorcin" by W. R. Orndorff et al.; printed in *American Chemical Journal*, vol. XLIV No. 1 ©1910.

*Primary Examiner*—Richard L. Raymond

[57] ABSTRACT

The present invention is a method of preparing a 4,6-bisarylazoresorcinol comprising reacting an aryldiazonium salt and resorcinol in the presence of a base and a reaction medium containing water and a water-miscible solvent at a temperature in the range of about −5° C to about −60° C. The present invention is also a method of preparing a 2-substituted 4,6-bisarylazoresorcinol comprising reacting an aryldiazonium salt with a 2-substituted resorcinol. The 4,6-bisarylazoresorcinol or 2-substituted 4,6-bisarylazoresorcinol can then be hydrogenated to a 4,6-diaminoresorcinol, which is a precursor to polybisbenzoxazoles (PBOs), polymers which are useful as insulators, solar arrays, and tear-resistant gloves.

17 Claims, No Drawings

1

PREPARATION OF 4,6-DIAMINORESORCINOL THROUGH A BISAZOARYLRESORCINOL INTERMEDIATE

BACKGROUND OF THE INVENTION

This invention relates to a process for preparing 4,6-diamino-1,3-benzenediols (4,6-diaminoresorcinols). More specifically, it relates to the preparation of 4,6-diaminoresorcinols starting with 1,3-benzenediols (resorcinols).

Diaminoresorcinols are used to prepare polybenzoxazoles (PBOs), the utility of which is discussed by, for example, Wolfe in Mark et al., *The Encyclopedia of Polymer Science and Engineering*, Volume 11, pp. 601–635, Wiley-InterScience Publication, New York, 1988. One of the more efficient and economical methods of preparing 4,6-diaminoresorcinol is described by Lysenko (U.S. Pat. No. 4,766,244, herein incorporated by reference), which reports the synthesis of the desired product in high purities and yields in three steps from 1,2,3-trichlorobenzene.

Halogenated aromatic compounds have become the subject of close environmental scrutiny in recent years. Thus, the once inexpensive and plentiful 1,2,3-trichlorobenzene is becoming expensive and hard to obtain. The questionable long-term availability of 1,2,3-trichlorobenzene requires that an inexpensive commodity starting material be found to prepare 4,6-diaminoresorcinol.

Lysenko et al. addresses this problem somewhat in U.S. Pat. No. 4,982,001, herein incorporated by reference, by preparing 4,6-diaminoresorcinol from the inexpensive and readily available resorcinol through a 1,3-bis(methylcarbonato)benzene intermediate. The steric hindrance of this intermediate causes nitration to take place mostly at the 4- and 6-positions, so that the desired 4,6-diaminoresorcinol can be prepared upon hydrolysis and hydrogenation. Unfortunately, a significant degree of undesirable nitration occurs at the 2-position of the intermediate, and there is the danger of forming the potentially adversely reactive styphnic acid.

Zollinger et al. (*Helvetica Chimica Acta*, Volume XLI, pp. 1816–1823 (1958), herein incorporated by reference) reports that 4,6-bisphenylazoresorcinol can be prepared from resorcinol and benzenediazonium chloride under basic conditions, using 0.1 weight percent resorcinol based on the weight of a buffered aqueous solution.

This 4,6-bisphenylazoresorcinol can be reduced to the corresponding 4,6-diaminoresorcinol, as shown over 100 years ago by Liebermann and Kostanecki (*Berichte der Deutschen Chemischen Gesellschaft*, Volume XX, pp. 3114–3119 (1888), herein incorporated by reference).

Because the reaction between resorcinol and phenyl diazonium salts is so rapid, it is difficult to avoid making the undesirable side-product, 2,4,6-trisphenylazoresorcinol. Zollinger avoids this problem somewhat, though not entirely, by keeping the initial concentration of resorcinol at about 0.1 weight percent based on the weight of solvent. Though this approach may be practical for preparing 4,6-bisphenylazoresorcinols on a laboratory scale, process scale preparations require higher reagent concentrations than Zollinger contemplates. The challenge, then, becomes maintaining or improving upon, at concentrations above about 0.5 weight percent loading of resorcinol, the yield and selectivity of 4,6-bisphenylazoresorcinol achieved at lower concentrations.

SUMMARY OF THE INVENTION

The present invention is a method of preparing a 4,6-bisarylazoresorcinol comprising reacting an aryldiazonium salt and resorcinol in the presence of a base and a reaction medium containing water and a water-miscible solvent at a temperature in the range of about −5° C. to about −60° C.

Another aspect of the present invention is a method of preparing a 2-substituted 4,6-bisarylazoresorcinol comprising reacting an aryldiazonium salt and a 2-substituted resorcinol.

A further aspect of the present invention is a compound of the general formula:

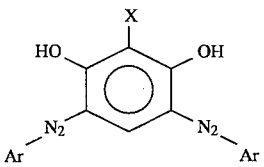

where X is chloro, bromo, or n-alkyl; and Ar is an aryl group.

The present invention addresses the deficiencies of the art by preparing 4,6-diaminoresorcinol not only in high yields (greater than 60 percent overall yield) and with high selectivity, but using initial concentrations of resorcinol substantially higher than contemplated by Zollinger et al., supra.

DETAILED DESCRIPTION OF THE INVENTION

In one aspect of the present invention, a 4,6-bisarylazoresorcinol is prepared by reacting an aryldiazonium salt and resorcinol in the presence of a base and a reaction medium at a temperature in the range of about −5° C. to about −60° C. Surprisingly, it has been discovered that high yields of the desired product can be obtained, starting with high concentrations of resorcinol, when the reaction is carried out in the specified temperature range.

Any aryldiazonium salt that will react with resorcinol to form the corresponding 4,6-bisarylazoresorcinol may be used. Preferred aryldiazonium salts include phenyldiazonium salts, naphthyldiazonium salts, anthryldiazonium salts, and phenanthryldiazonium salts. More preferred aryldiazonium salts are benzenediazonium salts, such as benzenediazonium chloride, benzenediazonium bromide, benzenediazonium chloride sulfonic acid, benzenediazonium bromide sulfonic acid, carboxybenzenediazonium chloride, carboxybenzenediazonium bromide, toluenediazonium chloride, and toluenediazonium bromide; the most preferred benzenediazonium salt is benzenediazonium chloride.

The aryldiazonium salt and resorcinol are advantageously dissolved together in sufficient quantities of a first solvent containing water to effect dissolution, then added to the base and a second solvent containing a water-miscible organic solvent at such a rate to control the resulting exotherm. The first solvent is advantageously maintained at a temperature of about 0° C., and the temperature of the second solvent is maintained at a temperature in the range of about −5° C. to about −60° C. The rate of addition of the first solvent to the second solvent is such that the temperature of the reaction medium is maintained in the range of about −5° C. to about −60° C.

Though the first solvent is preferably water, it may also contain one or more water-miscible organic solvent, preferably a water-miscible organic solvent having a boiling point less than 100° C. More preferred water-miscible organic solvents include ethanol, methanol, and acetone or a combination thereof.

The second solvent comprises a water-miscible organic solvent, preferably having a boiling point less than 100° C., more preferably methanol, ethanol, acetone, or a combination thereof. Most preferably, the second solvent comprises methanol and preferably not more than 60 weight percent water; more preferably not more than 30 weight percent water; and most preferably, methanol that is substantially water-free. Preferably, the w/w ratio of the first solvent to the second solvent is not more than 1:1, more preferably, not more than 1:5, most preferably, not more than 1:10. In combination, the first and second solvent form the reaction medium. The reaction medium preferably comprises methanol and not more than 80 weight percent water, more preferably methanol and not more than 50 weight percent water, most preferably methanol and not more than 20 weight percent water. The reaction medium is further characterized by having a freezing point below about −10° C., more preferably below −30° C., most preferably below about −60° C. The reagents and the base are essentially completely soluble in the reaction medium at the reaction temperatures (discussed herein).

The mole ratio of the aryldiazonium salt to resorcinol is preferably in the range of about 1.8:1 to about 2.2:1, more preferably in the range of 1.9:1 to about 2.1:1, most preferably in the range of about 1.95:1 to about 2.05:1. The initial concentration of resorcinol in the reaction medium is preferably at least about 0.5 weight percent, more preferably at least about 1 weight percent, most preferably at least about 1.7 weight percent based on the weight of the medium.

The base is a reagent that maintains the reaction at a pH of greater than 7. More preferably, the base is of such a strength, and used in such a concentration to maintain the reaction at a pH in the range of about 10 to about 14; most preferably from about 11 to about 13. The base is preferably sodium hydroxide, lithium hydroxide, tetrabutylammonium hydroxide, or potassium hydroxide, with sodium hydroxide being more preferred.

The reaction between the aryldiazonium salt and resorcinol is carried out at a temperature in the range of about −5° C., more preferably from about −10° C., most preferably from about −15° C.; to about −60° C., more preferably to about −40° C., and most preferably to about −30° C. The reaction is quite rapid, and tends to go to completion in the order of minutes.

Any 2,4,6-trisarylazoresorcinol that may form perferably precipitates out of solution and can be filtered away from the desired product, which remains dissolved in the reaction medium. The filtrate can then be acidified to precipitate the 4,6-bisarylazoresorcinol and the 4-arylazoresorcinol byproduct. The 4,6-bisarylazoresorcinol can be purified by recrystallization in a suitable solvent such as a mixture of chloroform and ethanol, thereby removing the 4-arylazoresorcinol.

The process of this aspect of the present invention reduces the levels of the 2,4,6-trisarylazoresorcinols compared to the processes of the prior art, thereby providing greater yields of the desired 4,6-bisarylazoresorcinol, and at higher concentrations than demonstrated by Zollinger et al., supra.

The 4,6-bisarylazoresorcinol, preferably 4,6-bisphenylazoresorcinol, is useful as an intermediate to 4,6-diaminoresorcinol, as discussed below.

Reaction of an Aryldiazonium Salt With a 2-Substituted Resorcinol

A further aspect of the present invention is a method of preparing a 2-substituted 4,6-bisarylazoresorcinol comprising reacting an aryldiazonium salt and a 2-substituted resorcinol. The term 2-substituted refers to a substituent at the 2-position of resorcinol, specifically one that does not adversely react with the aryldiazonium salt. The preferred 2-substituted resorcinols are 2-haloresorcinols and 2-n-alkylresorcinols; more preferred are 2-chlororesorcinol, 2-bromoresorcinol, and 2-methylresorcinol.

In this aspect of the invention, the undesirable by-product, trisarylazoresorcinol, cannot form due to the protecting group on the 2-position of resorcinol. Thus, the reaction conditions, including the mode of addition, the nature of solvents used, the concentration of reagents, and the pH and temperature of the reaction are not critical in this aspect of the invention. The reaction is preferably carried out in water, preferably at a temperature ranging from ambient temperature to about 0° C. The preferred molar ratio of aryldiazonium salt to 2-substituted resorcinol is about 2:1, but a ratio in excess of 2:1 is acceptable. The reaction can be carried out under acidic, basic, or neutral conditions, with basic conditions being preferred. The reaction times will vary depending primarily on the pH. Generally, the lower the pH, the slower the reaction.

Hydrogenation of 4,6-Bisarylazoresorcinol or a 2-Substituted 4,6-Bisarylazoresorcinol to 4,6-Diaminoresorcinol or a 2-Substituted 4,6-Diaminoresorcinol The 4,6-bisarylazoresorcinol or 2-chloro-4,6-bisarylazoresorcinol can be hydrogenated to 4,6-diaminoresorcinol. Similarly, the 2-alkyl-4,6-bisarylazoresorcinol can be hydrogenated to a 2-alkyl-4,6-diaminoresorcinol. The hydrogenating agent can be any agent which will supply hydrogen to the reaction. Suitable hydrogenating agents include borane; metal reducing agents in acids, such as zinc and HCl; $Na_2S_2O_4$; and hydrogen over a catalyst. (See March, *Advanced Organic Chemistry*, 4th Edition, John Wiley and Sons, (1992) page 1224, herein incorporated by reference.) Hydrogen over a catalyst is preferred. Preferred catalysts include platinum, palladium over carbon, and Raney nickel; more preferred are palladium over carbon and Raney nickel.

In the preferred process using hydrogen over a catalyst, the catalyst is used in an amount sufficient to catalyze the conversion of 4,6-bisarylazoresorcinol in the presence of hydrogen to the corresponding diaminoresorcinol. Preferably, about 0.001 to about 1 molar equivalents, more preferably from about 0.01 to about 0.5 molar equivalents, and most preferably from about 0.01 to about 0.1 molar equivalents of catalyst per equivalent of the initial concentration of the 4,6-bisarylazoresorcinol is used. The catalyst does not appear to lose activity over the course of several reactions. Thus, the catalyst may be recycled.

The hydrogenation reaction can be carried out over a large pressure range, though hydrogenation of the 4,6-bisarylazoresorcinol or the 2-alkyl-4,6-bisarylazoresorcinol is preferably carried out at low pressures, more preferably in the range of about 1 to about 4 atmospheres of hydrogen, most preferably at about 1 atmosphere; in contrast, hydrogenation of the 2-halo-4,6-bisarylazoresorcinol is preferably carried out at pressures in the range of 100 to 400 psi in accordance with Lysenko, supra.

In general, the hydrogenation reaction is carried out at a sufficiently high temperature to promote hydrogenation, yet sufficiently low to inhibit the decomposition of the desired product. The temperature is preferably maintained in the range of ambient temperature to about 100° C., more preferably from about 40° C. to about 75° C.

The hydrogenation reaction is advantageously carried out in the presence of a solvent, preferably an aqueous solvent that optionally contains a cosolvent, such as ethanol or methanol. The reaction can be carried out under basic, neutral or acidic conditions (provided the catalyst is stable at the pH of the reaction) and for a time sufficient to reduce substantially all of the azo groups to amino groups. The reaction is preferably carried out under approximately neutral conditions and in the substantial absence of air.

The products of hydrogenation include 4,6-diaminoresorcinol or 2-alkyl-4,6-diaminoresorcinol (hereinafter referred to as the diaminoresorcinol) and a primary aromatic amine. (In the reduction of the 2-halo-4,6-diarylazoresorcinol, the halo group is replaced with hydrogen, whereas in the reduction of the 2-alkyl-4,6-diarylazoresorcinol, the alkyl group is not replaced.) Upon the completion of the reaction and before the product is exposed to air, the product mixture is advantageously acidified to form a quaternary ammonium salt, which is more stable to oxidation than the free base. Hydrochloric acid is suitable for such purpose. The consequent quaternary ammonium salt of the diaminoresorcinol may be separated from the quaternary ammonium salt of the primary aromatic amine in a number of ways.

One method of separating the aromatic amine from the diaminoresorcinol is to add sufficient acid to selectively form the monoquaternary ammonium salt of diaminoresorcinol, yet insufficient to form the quaternary ammonium salt of the primary aromatic amine. This is possible because the $pk_a$ of the primary aromatic amine is about 2 $pk_a$ units higher than the first $pk_a$ of the diaminoresorcinol.

A preferred way of carrying out this selective quaternization is to add under an inert atmosphere sufficient acid, preferably hydrochloric acid, to form the monoquaternary ammonium salt of the diaminoresorcinol, yet insufficient to form the diquaternary salt. During this addition, some quaternary ammonium salt of the primary aromatic amine may form. The solvent can then be removed, preferably in vacuo and in the substantial absence of air, after which sufficient base, preferably sodium hydroxide, can be added to convert any quaternary ammonium salt of the primary aromatic amine to the corresponding free base. This free base can then be removed, for example, by steam distillation.

Another method of separating the aromatic amine from the diaminoresorcinol is to add sufficient acid to the product mixture to form the diquaternary ammonium salt of diaminoresorcinol and the quaternary ammonium salt of the primary aromatic amine; remove the solvent, preferably in vacuo and in the substantial absence of air; then recrystallize the diquaternary ammonium salt of diaminoresorcinol in a solvent in which the quaternary ammonium salt of the primary aromatic amine is soluble at ambient temperatures. The recrystallizing solvent is preferably a concentrated inorganic protic acid, and more preferably from about 3N to about 12N hydrochloric acid.

In each of the above methods of isolating the desired diaminoresorcinol, a small amount of an antioxidant, such as $SnCl_2$ can be added along with the acid to inhibit oxidation of the diaminoresorcinol.

The products of this invention are useful as precursors to polybisbenzoxazoles (PBOs), polymers which are useful as insulators, solar arrays, and tear-resistant gloves. PBOs can be prepared by reacting 4,6-diaminoresorcinol with bisacids, bisacid halides, bisesters, or bisnitriles. (See Wolfe, supra.)

The following examples are provided to illustrate the invention, but are not intended to limit the scope thereof. All parts and percentages are by weight unless otherwise indicated.

EXAMPLE 1

Preparation of 4,6-Bisphenylazoresorcinol

Concentrated aqueous HCl (5 mL) is added to a slurry of aniline (1.88 g, 0.02 mol) in water (15 mL). The resultant anilinium hydrochloride is cooled to 0° C. and an aqueous solution of sodium nitrite (1.38 g, 0.02 mol in 5 mL water) is added thereto. The resultant phenyldiazonium chloride is combined with resorcinol (1.1 g, 0.01 mol), diluted to approximately 40 mL total volume with methanol, and slowly added to a −25° C. solution of sodium hydroxide (3 g) in methanol (120 mL). The total volume of the reaction medium is 160 mL, which also contains 12% water, a 2% load of theoretical product, and a 0.7% load of resorcinol. When the addition is complete, the methanol is removed by rotary evaporation, about 100 mL of water is added, and the remaining aqueous slurry is filtered through a celite plug. Concentrated HCl is added to the filtrate (to below pH 3) and the precipitate is filtered to give crude 4,6-bisphenylazoresorcinol (3 g) as a red solid. The material is recrystallized from chloroform/ethanol (40 mL/10 mL) to give pure 4,6-bisphenylazoresorcinol as red needles (2.35 g, 73%).

EXAMPLE 2

Preparation of 4,6-Bis(phenylazo)-2-methylresorcinol

A 0.5 L 3-necked flask (flask 1), equipped with a magnetic stirring bar and a thermometer protruding to the bottom, is charged with 2-methylresorcinol (1.24 g, 10 mmol), $H_2O$ (300 mL), and NaOH (4.5 g, 112.5 mmol). The mixture is stirred vigorously until a homogeneous solution results, then is cooled in an ice-water bath to 0° C. to 2° C. Meanwhile, a 50 mL 3-necked flask (flask 2), equipped with a magnetic stirring bar and a thermometer protruding to the bottom, is charged with aniline (1.88 g, 20.2 mmol) and $H_2O$ (6 mL), and the mixture is stirred rapidly and cooled in an ice-water bath while concentrated HCl (6 mL, 59 mmol) is added dropwise. Then, an ice-cold solution of $NaNO_2$ (1.38 g, 20 mmol) in $H_2O$ (5 mL) is added slowly dropwise while maintaining the temperature at <5° C., and the solution is diluted with ice-cold water (25 mL). The resulting solution in flask 2 is added dropwise to the vigorously stirred solution in flask 1 at such a rate that the temperature is maintained at <5° C. After 15 minutes, the cooling bath is removed and stirring continued at ambient temperature for 1 hour. The resultant dark mixture is filtered under suction, and the solid that collects on the filter is washed with water (50 mL). The solid is dissolved in $CH_2Cl_2$ (100 mL), and filtered to remove any undissolved solids. The filtrate is diluted with MeOH (0.5 L) with stirring, resulting in the separation of a solid. The solid is collected by filtration and air-dried for 16 hours to give 2.6 g (78% yield) of product. The sample is greater than 99% pure 4,6-bis(phenylazo)- 2-methylresorcinol as determined by HPLC, proton and carbon NMR spectroscopy.

EXAMPLE 3

Preparation of 4,6-Diaminoresorcinol Dihydrochloride 4,6-Bisphenylazoresorcinol (2.5 g, 7.85 mmol), ethanol (100%, 70 mL), distilled water (30 mL), concentrated hydrochloric acid (36% to 38%, 2.6 mL) and palladium (10% on carbon, 0.15 g) are placed in a 250 mL round-bottom flask, equipped with a magnetic stirrer and an oil bath. The temperature of the oil bath rises to 55° C. and is maintained at that temperature. The reaction system is evacuated and filled with hydrogen three times, and then filled with hydrogen (1 L, STP). The stirring is started, and the hydrogenation proceeds until hydrogen uptake stops. At the end of the reaction, the original brown slurry has turned into a colorless aqueous suspension of the catalyst. The time required for hydrogenation is approximately 3 hours, during which time about 0.75 L of hydrogen (STP) is consumed. The reaction flask is disconnected from the hydrogenation apparatus and the mixture flushed with nitrogen for 2 minutes. A solution of stannous chloride dihydrate (0.2 g) in hydrochloric acid (5 mL) is added in one portion. The mixture is stirred for 1 minute and then filtered to remove the catalyst. The filtrate is transferred to a flask and solvent is removed by rotary evaporation. The ethanol is azeotroped and collected for recycling, and the remaining aqueous solution is dried under reduced pressure. The residual white solid is redissolved in hydrochloric acid (5N, 45 mL) and the resultant solution is heated at reflux for 10 minutes. The solution is then allowed to stand at ambient temperature overnight for crystallization. The product is collected by filtration on a fritted funnel, dried first under a stream of nitrogen and then in a vacuum oven at reduced pressure and 45° C. for 8 hours affording 4,6-diaminoresorcinol dihydrochloride as white flakes, 1.51 g, in 90% yield.

EXAMPLE 4

Preparation of 2-Methyl-4,6-diaminoresorcinol Dihydrochloride

The desired product is prepared using the same procedure as used in Example 3. In this example, 4,6-bis(phenylazo)-2-methylresorcinol (2.6 g, 7.82 mmol), ethanol (100%, 70 mL), distilled water (30 mL), concentrated hydrochloric acid (36–38%, 2.6 mL) and palladium on carbon (10%, 0.15 g) are used. The yield of desired 2-methyl-4,6-diaminoresorcinol dihydrochloride is 1.44 g (81% yield).

What is claimed is:

1. A method of preparing a 4,6-bisarylazoresorcinol comprising reacting an aryldiazonium salt and resorcinol in the presence of a base and a reaction medium containing water and a water-miscible solvent at a temperature in the range of about −5° C. to about −60° C., wherein the initial concentration of resorcinol is at least 0.5 weight percent based on the weight of the reaction medium.

2. The method of claim 1 wherein the reaction medium contains not more than 80 weight percent water based on the weight of the reaction medium.

3. The method of claim 2 wherein the reaction medium comprises not more than 50 weight percent water.

4. The method of claim 3 wherein the initial concentration of resorcinol is at least 0.7 weight percent based on the weight of the reaction medium.

5. The method of claim 4 wherein the contacting temperature is maintained in the range of about −10° C. to about −30° C.

6. The method of claim 5 wherein the aryldiazonium salt and resorcinol are dissolved together in water, then added to the base and the water-miscible solvent.

7. The method of claim 6 wherein the water-miscible solvent is methanol.

8. The method of claim 7 wherein the base is sodium hydroxide.

9. The method of claim 8 wherein the aryldiazonium salt is benzenediazonium chloride.

10. The method of claim 1 further comprising the step of reacting the 4,6-bisarylazoresorcinol with a hydrogenating agent to form a 4,6-diaminoresorcinol.

11. The method of claim 10 wherein the hydrogenating agent is hydrogen over a catalyst.

12. The method of claim 11 wherein the catalyst is Raney nickel or palladium.

13. The method of claim 1 wherein the water-miscible solvent is selected from the group consisting of methanol, ethanol, and acetone.

14. A method comprising the steps of:
   a) reacting an aryldiazonium salt with a 2-n-alkylresorcinol to form a 2-n-alkyl-4,6-bisarylazoresorcinol; and
   b) reacting the 2-alkyl 4,6-bisarylazoresorcinol with a hydrogenating agent to form a 2-n-alkyl-4,6-diaminoresorcinol.

15. The method of claim 14 wherein the 2-substituted resorcinol is 2-methylresorcinol, 2-chlororesorcinol, or 2-bromoresorcinol.

16. The method of claim 15 wherein the 2-substituted resorcinol is 2-methylresorcinol, and the 2-substituted-4,6-bisarylazoresorcinol is 2-methyl-4,6-bisphenylazoresorcinol.

17. The method of claim 14 where the hydrogenating reagent is hydrogen over a catalyst.

* * * * *